United States Patent [19]
Muders et al.

[11] 4,213,910
[45] * Jul. 22, 1980

[54] PROCESS FOR THE PREPARATION OF 1-AMINO-4-BROMOANTHRAQUINONE-2-SULPHONIC ACID I

[75] Inventors: Rolf Muders, Cologne; Heinrich Leister; Helmut Dittmer, both of Leverkusen; Hubert Schönhagen, Odenthal, all of Fed. Rep. of Germany

[73] Assignee: Bayer Aktiengesellschaft, Leverkusen, Fed. Rep. of Germany

[ * ] Notice: The portion of the term of this patent subsequent to Jul. 22, 1997, has been disclaimed.

[21] Appl. No.: 939,715

[22] Filed: Sep. 5, 1978

[30] Foreign Application Priority Data

Sep. 10, 1977 [DE] Fed. Rep. of Germany ....... 2740885

[51] Int. Cl.² .......................................... C07C 143/63
[52] U.S. Cl. .................................................... 260/371
[58] Field of Search ......................................... 260/371

[56] References Cited

U.S. PATENT DOCUMENTS

| | | | |
|---|---|---|---|
| 1,841,997 | 1/1932 | Weinand | 260/371 |
| 2,413,790 | 1/1947 | Seymour et al. | 260/371 |

FOREIGN PATENT DOCUMENTS

| | | |
|---|---|---|
| 5459 of 1901 | United Kingdom | 260/371 |
| 1291225 10/1972 | United Kingdom | 260/371 |

OTHER PUBLICATIONS

*Chemical Abstract*, vol. 82, #31183; "1-Amino-4-bromoanthraquinone" Nakahara 7/24/74.

*Primary Examiner*—Winston A. Douglas
*Assistant Examiner*—Raymond K. Covington
*Attorney, Agent, or Firm*—Sprung, Felfe, Horn, Lynch & Kramer

[57] ABSTRACT

A process for preparing 1-amino-4-bromoanthraquinone-2-sulphonic acid or an alkali metal salt thereof which comprises contacting 1-amino-anthraquinone at a temperature in the range of 90° to 150° C. with an $SO_3$-containing sulphuric acid (oleum) and thereafter treating the resultant sulphonated 1-amino-anthraquinone with at least 0.5 molar equivalent of bromine, relative to 1 mol of 1-amino-anthraquinone, at temperatures in the range from 60° to 100° C.

11 Claims, No Drawings

PROCESS FOR THE PREPARATION OF 1-AMINO-4-BROMOANTHRAQUINONE-2-SULPHONIC ACID I

The invention relates to a process for the preparation of 1-amino-4-bromoanthraquinone-2-sulphonic acid from 1-amino-anthraquinone.

The preparation of 1-amino-4-bromoanthraquinone-2-sulphonic acid is usually carried out in a 2-stage process, the sulphonation of the 1-amino-anthraquinone with chlorosulphonic acid in a water-immiscible inert organic solvent being carried out in stage 1. After separating off the organic solvent, bromination is then carried out in a neutral aqueous solution (compare, for example, U.S. Pat. No. 3,428,659) or in a solution containing sulphuric acid (compare, for example, Japanese Laid-Open Specification No. 49,076,848).

Another two-stage route consists in first sulphonating 1-amino-antraquinone in $SO_3$-containing sulphuric acid (compare German Pat. No. 263,395 and 484,997), isolating the resulting 1-amino-anthraquinone-2-sulphonic acid and carrying out the bromination in an aqueous medium (compare, for example, FIAT 1313 II, page 214, U.S. Pat. Nos. 2,413,790, 2,440,760 and 2,503,254 and DI-AS (German Published Specification) 2,303,246).

According to the process described in German Pat. No. 2,551,767, boric acid is also added during the sulphonation. The bromination is carried out in very dilute aqueous sulphuric acid.

In the processes mentioned, the aminosulphonic acid is intermediately isolated or extracted, which means an additional process step, making the process require technical effort.

A process has now been found for the preparation of 1-amino-4-bromoanthraquinone-2-sulphonic acid from 1-amino-anthraquinone, which is characterised in that 1-amino-anthraquinone is heated to temperatures in the range from 90° to 150° C. with $SO_3$-containing sulphuric acid, alkali metal sulphates being added if necessary, and the mixture is then treated with at least 0.5 molar equivalent of bromine, relative to 1 mol of 1-amino-anthraquinone, at temperatures in the range from 60°–100° C. 1-Amino-4-bromoanthraquinone-2-sulphonic acid is obtained in good yields (over 70% of theory) and high purity (at least 93%) in the process according to the invention, without intermediate isolation of the 1-aminoanthraquinone-2-sulphonic acid.

As a rule, the sulphonation in the process according to the invention is carried out by dissolving the 1-aminoanthraquinone in the $SO_3$-containing sulphuric acid, adding alkali metal sulphate if necessary, and bringing the reaction mixture to the desired temperature, or by introducing the components into pure or $SO_3$-containing sulphuric acid and completing the sulphonation by adding $SO_3$-containing sulphuric acid ("$SO_3$-containing sulphuric acid" is called "oleum" normally).

The amount of sulphuric acid employed can be varied within wide limits. The sulphuric acid is customarily used in an amount such that the reaction mixture remains stirrable, for example in 2 to 8 times the amount by weight, preferably in 2 to 4 times the amount by weight, relative to 1-amino-anthraquinone employed.

The $SO_3$ content of the sulphuric acid should be high enough to carry out virtually quantitative sulphonation in the 2-position. On the other hand, too high $SO_3$ concentration can lead to introduction of further sulphonic acid groups. In general, the $SO_3$ content of the sulphuric acid to be used for the sulphonation is about 4 to 40% by weight, preferably 10 to 25% by weight, relative to 100% strength by weight sulphuric acid.

The temperature required during the sulphonation depends to a large extent on the chosen concentration of $SO_3$. It is in the range from about 90° to 150° C., and is preferably 100° to 140° C. High temperatures, for example about 135° to 150° C., are advantageously used with low $SO_3$ concentrations (10–15%), and low temperatures, for example 100° to 120° C., are advantageously used with high $SO_3$ concentrations (20–25%). It is advisable first of all to start the sulfonation by introducing a small amount of $SO_3$-containing sulphuric acid into the reactor and adding more $SO_3$-containing sulphuric acid to end the reaction.

Alkali metal sulphates, such as lithium sulphate, sodium sulphate, potassium sulphate, rubidium sulphate and caecium sulphate, preferably sodium sulphate and/or potassium sulphate can be advantageously added to the sulphonation mixture. The alkali metal salt addition is intended to prevent not only the entry of a further sulphonic acid group, but also hydroxylation in the 4-position. Anhydrous sulphates are preferably used.

In general, 0.1 to 1.4 parts, preferably 0.4 to 1.2 parts, of alkali metal sulphate per part of 1-aminoanthraquinone are added to the sulphonation mixture. Without the addition of or in the presence of only a small amount of alkali metal sulphate higher proportions of 1-aminoanthraquinone-2,4-disulphonic acid are generally obtained than with the addition of approximately the same amount of alkali metal sulphate as that of 1-aminoanthraquinone.

Any 1-amino-anthraquinone-2,4-disulphonic acid formed during the sulphonation does not affect the further course of the reaction, since the 4-sulphonic acid group is eliminated again as the sulphuric acid concentration gradually falls, or is later replaced by bromine. This elimination can be accelerated if the sulphuric acid concentration is lowered to about 95 to 100% by weight after the sulphonation.

The course of the sulphonation can be readily followed by chromatography. In general, the sulphonation has ended after about 1 to 10 hours, preferably after 2 to 6 hours.

The bromination following the sulphonation is carried out at lower temperatures, for example in the range from about 60° to 100° C., preferably at 70° to 90° C. The reaction mixture must therefore be cooled to the desired bromination temperature before the bromine addition.

It is advantageous to add a customary halogenation catalyst, such as iodine, for the bromination. However, the addition of such a catalyst is not absolutely necessary for the process according to the invention.

Since a large proportion of the hydrogen bromide formed during the bromination is re-oxidized to bromine in the reaction mixture, less than 1 molar equivalent of bromine is consumed per mol of 1-aminoanthraquinone employed. At least 0.5 molar equivalent, in general 0.6 to 0.9 molar equivalent, of bromine, and preferably 0.6 to 0.7 molar equivalent of bromine, relative to 1 mol of 1-amino-anthraquinone, is required.

The bromination can be carried out under normal pressure, with reflux cooling, or under pressure. It is usually carried out under normal pressure, but it can sometimes be advantageous to operate under a pressure of up to about 6 bars.

The course of the bromination can also be readily followed by chromatography. In general, the bromination has ended after about 4 to 16 hours.

The reaction mixture can be worked up advantageously by adjusting the sulphuric acid concentration of the reaction mixture to about 60 to 85% by weight, preferably 65 to 80% by weight, by mixing with water or dilute sulphuric acid after excess bromine has been removed. It is advisable first of all to start the addition with sulphuric acid of a somewhat higher concentration (for example 70% strength). During this procedure, the 1-amino-4-bromoanthraquinone-2-sulphonic acid separates as the sulphate. The precipitation temperature is about 50° to 60° C., and can be increased by a further 30° to 40° C. in order to improve the form in which the material is filtered off. The precipitated sulphate is isolated by filtration and freed from the adhering mother liquor by washing with about 60 to 85% strength sulphuric acid.

The sulphate thus obtained is hydrolysed by stirring with water, the 1-amino-4-anthraquinone-2-sulphonic acid being precipitated as a salt by adding alkali metal salts, such as sodium chloride, potassium chloride, sodium sulphate and/or potassium sulphate, or alkalies, such as sodium hydroxide solution or potassium hydroxide solution or sodium carbonate.

This type of working up gives favorable preconditions for processing the sulphuric acid obtained, the concentration of which is more than 60% by weight, by known methods of concentration.

Another way of working up the reaction mixture after the bromination consists in pouring the mixture, whilst stirring, into water or ice-water, to which sodium chloride, potassium chloride, sodium sulphate and/or potassium sulphate has been appropriately added. The 1-amino-4-bromoanthraquinone-2-sulphonic acid which has precipitated is isolated from the acid suspension by filtration. Depending on the course of the reaction, up to a total of 5% of impurities, consisting of small amounts of by-products, such as 1-amino-2- or -4-bromoanthraquinone, 1-amino-2,4-dibromoanthraquinone and 1-amino-anthraquinone-2-sulphonic acid, adhere to the material being filtered.

The water-insoluble constituents are separated off by clarifying filtration of the reaction product, dissolved in water, in the acid and/or alkaline range, advantageously in the presence of filtration auxiliaries, such as active charcoal or kieselguhr.

The 1-amino-4-bromoanthraquinone-2-sulphonic acid can be precipitated from the filtrate in the form of its alkali metal salt by salting out, for example with sodium chloride, potassium chloride, sodium sulphate and/or potassium sulphate. The 1-amino-4-bromoanthraquinone-2-sulphonic acid is isolated by filtration and rinsed with dilute salt solution, and the product thus obtained is dried.

The advantage of the process according to the invention is the single-stage procedure. This makes the process according to the invention particularly economical. The physical nature and the quality of the 1-aminoanthraquinone employed do not affect the course of the reaction. 1-Amino-4-bromoanthraquinone-2-sulphonic acid is an important intermediate product for numerous valuable dyestuffs (compare Ullmann Encyklopädie der technischen Chemie (Ullmann's Encyclopaedia of Industrial Chemistry), 4th edition, volume 7, page 639–640).

The examples which follow are intended to illustrate the process according to the invention in more detail, but without limiting it to these examples.

EXAMPLE 1

150 g of 96% strength 1-aminoanthraquinone are introduced into a mixture of 200 ml of 20% strength oleum and 100 g of anhydrous sodium sulphate, whilst stirring, and the mixture is heated to 130° C. in the course of 1 hour. This temperature is maintained for 2 hours, 120 ml of 20% strength oleum and 50 g of anhydrous sodium sulphate are added and the mixture is stirred at 130° C. for a further 3 hours. The sulphonation has then virtually ended. For the bromination, the mixture is cooled to 80° C., 0.2 g of iodine and about 0.5 ml of an anti-foaming agent are added and 21 ml of bromine are allowed to run into the mixture, in portions, at 80° C. in the course of 9 hours. Thereafter, the content of 1-amino-anthraquinone-2-sulphonic acid in a sample which has been worked up is less than 1%.

For working up, excess bromine is first removed by evacuating the mixture for a short time, and 140 ml of water are then added dropwise in the course of 1 hour, the temperature rising from 80° C. to 110° C. The bromamineacid sulphate is filtered off at 50°0 to 60° C. and rinsed with 300 ml of 60% strength sulphuric acid. The mother liquor and wash liquor are combined and give 855 g of a 65% strength sulphuric acid, which can be concentrated by known processes.

The filter cake (668 g) is stirred into 1,800 ml of water, the pH value is adjusted to 8 by adding 308 ml of 50% strength sodium hydroxide solution and the mixture is heated to 90° C. for 1 hour. It is then cooled to 60° C. and the sodium salt of 1-amino-4-bromoanthraquinone-2-sulphonic acid is filtered off, washed with 1,200 ml of a 1.5% strength sodium sulphate solution and dried. 234.6 g are obtained, with the following analysis: 87.5% of 1-amino-4-bromoanthraquinone-2-sulphonic acid, 0.5% of 1-amino-anthraquinone-2-sulphonic acid, 0.4% of non-sulphonated constituents and 7.1% of water.

The yield of 1-amino-4-bromoanthraquinone-2-sulphonic acid is accordingly 83.2% of theory, relative to 1-aminoanthraquinone.

The purity of the 1-amino-4-bromoanthraquinone-2-sulphonic acid is 94.2%, based on the anhydrous substance.

EXAMPLE 2

146 g of anhydrous sodium sulphate and 150 g of 1-aminoanthraquinone are introduced into 260 ml of 100% strength sulphuric acid, whilst stirring, and are dissolved at 80° to 85° C. For the sulphonation, the solution is heated to 120° C. and 94 ml of 65% strength oleum are then added uniformly in the course of 3 hours. After stirring the mixture for a further two hours, the sulphonation has ended, which can be followed by chromatography in accordance with the customary method.

For the bromination, the mixture is cooled to 50° C. and diluted with 18 ml of 78% strength sulphuric acid, and 0.8 g of iodine, together with 73 g of bromine, are added. The reaction mixture is heated under reflux to 60° C. for 6 hours, the sulphuric acid concentration of the reaction mixture is then adjusted to 95% by adding dilute sulphuric acid and bromination is carried out at 60° to 70° C. for a further 12 hours.

The further working up is carried out by the procedure described in Example 1, by precipitating and isolating the sulphate from the solution containing sulphuric acid, and subsequent hydrolysis, the 1-amino-4-bromoanthraquinone-2-sulphonic acid being obtained in the same quality and yield as in Example 1.

EXAMPLE 3

The sulphonation and bromination are carried out as described in Example 1 or 2.

For working up, excess bromine is removed from the reaction melt by evacuating for a short time and the concentration of the sulphuric acid in the reaction mixture is adjusted to about 70% by slowly adding 30% strength sulphuric acid. The sulphate of 1-amino-4-bromoanthraquinone-2-sulphonic acid thereby precipitates and is filtered off and washed with 300 ml of 60% strength sulphuric acid. The collected filtration runnings contain 65 to 68% of sulphuric acid, which can be concentrated in accordance with the customary method.

The material from the filtration is stirred into 300 ml of water and filtered off again. The filtrate obtained, with a sulphuric acid content of 30%, serves, in the manner of a recycling process, for diluting the reaction melt as described above.

For neutralisation, the 1-amino-4-bromoanthraquinone-2-sulphonic acid isolated is stirred into 2,000 ml of water and the suspension is adjusted to pH 9 with 50% strength sodium hydroxide solution. The mixture is heated to 90° C. for 15 minutes, whilst stirring, cooled to 50° to 60° C. and filtered and the residue is washed with a 1.5% strength aqueous sodium sulphate solution.

The yield and quality of the product thus obtained are as described under Example 1.

EXAMPLE 4

The sulphonation and bromination are carried out as under Example 1 or 2 and the reaction mixture is worked up as follows:

The reaction mixture is cooled to 20° C. and introduced, whilst stirring, into 1,200 g of ice-water, in which 27 g of sodium chloride are dissolved. The 1-amino-4-bromoanthraquinone-2-sulphonic acid thus precipitated is filtered off and stirred into 3,000 ml of water. The pH value is adjusted to 8 to 9 by adding 50% strength sodium hydroxide solution. On heating the mixture to 95° to 100° C., a solution is obtained. 12 g of a mixture of active charcoal and kieselguhr are added and the mixture is kept at the above temperature for a further ½ hour and filtered hot. The filtration residue is washed with 400 ml of hot water.

The salt of 1-amino-4-bromoanthraquinone-2-sulphonic acid is precipitated from the collected filtrates at 90° to 95° C. with 50 g of sodium sulphate. Before the filtration, the mixture is cooled to 40° C.

1-Amino-4-bromoanthraquinone-2-sulphonic acid is obtained in a purity of 93 to 94%, based on anhydrous substance, and in more than 70% yield.

EXAMPLE 5

20 g of anhydrous sodium sulphate are dissolved in 150 ml of 20% strength oleum, and 150 g of 1-aminoanthraquinone are introduced into the solution below 60° C. The reaction mixture is heated to 110° C. for 3 hours, cooled to 80° C. and, after adding 55 ml of 20% strength oleum, is heated to 110° C. for a further 3 hours. About 0.1–0.2 g of iodine are then added, and 24 ml of bromine are added slowly at 80° C. After about 16 hours, the bromination reaction is brought to completion by warming the reaction mixture under reflux to 80° C. The excess bromine is carefully removed by evacuation or bubbling out and the sulphate of 1-amino-4-bromoanthraquinone-2-sulphonic acid is precipitated by slowly diluting the mixture with 135 ml of 30% strength sulphuric acid. The precipitate is filtered off and washed with 300 ml of 70% strength sulphuric acid and then with 200 ml of 30% strength sulphuric acid. For the hydrolysis, the reaction product is stirred into 2,000 ml of water and the pH is adjusted to 1 at 95° C. with 25% strength sodium hydroxide solution. A solution is thereby obtained. After adding further sodium hydroxide solution to PH 7, the sodium salt of 1-amino-4-bromoanthraquinone-2-sulphonic acid crystallises out. The pH of the mixture is adjusted to 8–9 with a little sodium carbonate and the crystals are filtered off at 40°–60° C. and washed with a dilute sodium sulphate solution. Yield: 236 g of the sodium salt, with a purity of 86.7%.

EXAMPLE 6

150 g of 1-aminoanthraquinone are introduced into 150 ml of 20% strength oleum, whilst cooling (temperature <60° C.), and the reaction mixture is heated to 110° C. in the course of about 1 hour. This temperature is maintained for about 2 hours, 55 ml of 20% strength oleum are then slowly added at 90° C. and the sulphonation is continued at 110° C. After the reaction has ended (a period of at least 2 hours), the reaction mixture is brominated and worked up, as described under Example 5.

Yield: 226 g of the sodium salt with a purity of 86%.

EXAMPLE 7

The sulphonation is carried out as described in Example 5. For the bromination, 0.15 g of iodine and 62.5 g of bromine are added to the reaction mixture and the mixture is heated to 80° C. in a closed reaction vessel for 16 hours, whilst stirring. The pressure thereby increases to 3.5–4 bars. After cooling to 60° C., the reaction vessel is vented in order to then carefully remove excess bromine and hydrogen bromide from the reaction mixture by bubbling out or evacuation.

For the working up, 108 ml of 70% strength sulphuric acid and then 140 ml of 30% strength sulphuric acid are slowly added, whilst stirring, the 1-amino-4-bromoanthraquinone-2-sulphonic acid precipitating in the form of its sulphate. The precipitate is filtered off and washed with 375 ml of 70% strength sulphuric acid and with 234 ml of 30% strength sulphuric acid.

The further working up by hydrolysis is carried out as described under Example 5; the 1-amino-4-bromoanthraquinone-2-sulphonic acid being obtained in the same good quality and yield as in that example.

What we claim is:

1. A process for preparing 1-amino-4-bromoanthraquinone-2-sulphonic acid or an alkali metal salt thereof which comprises contacting 1-amino-anthraquinone at a temperature in the range of 90° to 150° C. with an $SO_3$-containing sulphuric acid (oleum) and thereafter treating the resultant sulphonated 1-amino-anthraquinone with at least 0.5 molar equivalent of bromine, relative to 1 mol of 1-amino-anthraquinone, at temperatures in the range from 60° to 100° C.

2. A process according to claim 1, wherein an alkali metal sulphate is present in the reaction mixture when said 1-amino-anthraquinone is heated at 90° to 150° C. in the presence of an SO$_3$-containing sulphuric acid.

3. A process according to claim 1 or 2, wherein the SO$_3$-content of the sulphuric acid is 4 to 40% by weight, relative to 100% strength by weight sulphuric acid.

4. A process according to claims 1, 2 or 3, wherein the SO$_3$-containing sulphuric acid is added in 2 to 8 times the amount by weight, relative to 1-amino-anthraquinone.

5. A process according to claim 2, wherein the alkali metal sulphate is sodium sulphate or potassium sulphate.

6. A process according to claim 2, wherein the alkali metal sulphate is employed in an amount of 0.1 to 1.4 parts by weight per part of 1-amino-anthraquinone.

7. A process according to claims 1, 2, 3, 4, 5 or 6 wherein the bromination is carried out with 0.6 to 0.9 molar equivalent of bromine, relative to 1 mol of 1-amino-anthraquinone.

8. A process according to claims 1, 2, 3, 4, 5, 6 or 7, wherein in order to isolate 1-amino-4-bromo-anthraquinone-2-sulphonic acid, sulphuric acid concentration in the reaction mixture is adjusted to 60 to 85% by weight by mixing the reaction mixture with water or dilute sulphuric acid, and the sulphate of 1-amino-4-bromo-anthraquinone-2-sulphonic acid which separates is filtered off and converted into 1-amino-4-bromo-anthraquinone-2-sulphonic acid and/or its alkali metal salt by the action of water and/or water which contains an alkaline substances.

9. A process according to claim 1 wherein bromination is effected with a brominating agent consisting essentially of bromine.

10. A process according to claim 9 wherein the bromination is effected without any intermediate isolation or extraction of the aminosulfonic acid formed by sulfonation of said 1-aminoanthraquinone.

11. A process according to claim 10 wherein in order to isolate 1-amino-4-bromoanthraquinone-2-sulfonic acid, the sulfuric acid concentration in the reaction mixture is adjusted to 60 to 85 percent by weight by mixing the reaction mixture with water or dilute sulfuric acid and the sulfate of 1-amino-4-bromoanthraquinone-2-sulfonic acid which separates is filtered off and converted to 1-amino-4-bromoanthraquinone-2-sulfonic acid and/or its alkali metal salt by the action of water and/or water which contains an alkaline substance.

* * * * *